US010359429B2

(12) United States Patent
Forsyth et al.

(10) Patent No.: US 10,359,429 B2
(45) Date of Patent: Jul. 23, 2019

(54) TAGGED LIGANDS FOR ENRICHMENT OF RARE ANALYTES FROM A MIXED SAMPLE

(71) Applicant: GPB Scientific, LLC, Richmond, VA (US)

(72) Inventors: Allyn Forsyth, San Diego, CA (US); Helen Barnes, San Diego, CA (US)

(73) Assignee: GPB Scientific, LLC, Richmond, VA (US)

( * ) Notice: Subject to any disclaimer, the term of this patent is extended or adjusted under 35 U.S.C. 154(b) by 0 days.

(21) Appl. No.: 14/995,894

(22) Filed: Jan. 14, 2016

(65) Prior Publication Data

US 2017/0023578 A1 Jan. 26, 2017

Related U.S. Application Data

(60) Continuation of application No. 14/103,352, filed on Dec. 11, 2013, now abandoned, which is a continuation of application No. 13/692,710, filed on Dec. 3, 2012, now abandoned, which is a continuation of application No. 13/182,003, filed on Jul. 13, 2001, now abandoned, which is a division of application No. 12/037,077, filed on Feb. 25, 2008, now Pat. No. 8,008,032.

(51) Int. Cl.

| | |
|---|---|
| ***G01N 33/574*** | (2006.01) |
| ***G01N 33/58*** | (2006.01) |
| ***G01N 33/543*** | (2006.01) |
| ***B01L 3/00*** | (2006.01) |
| ***G01N 1/40*** | (2006.01) |

(52) U.S. Cl.

CPC .. *G01N 33/57492* (2013.01); *B01L 3/502761* (2013.01); *G01N 1/405* (2013.01); *G01N 33/54326* (2013.01); *G01N 33/574* (2013.01); *G01N 33/585* (2013.01); *B01L 2200/0647* (2013.01); *B01L 2300/0861* (2013.01); *B01L 2400/086* (2013.01); *G01N 2333/705* (2013.01); *Y10S 435/971* (2013.01); *Y10S 435/973* (2013.01); *Y10T 436/101666* (2015.01); *Y10T 436/13* (2015.01); *Y10T 436/25125* (2015.01); *Y10T 436/25375* (2015.01)

(58) Field of Classification Search

CPC ........... G01N 33/57492; G01N 33/574; G01N 1/405; G01N 2333/705; B01L 3/502671; B01L 3/502761; B01L 2300/0861; B01L 2200/0647; Y10T 436/25375; Y10T 436/13; Y10T 436/25125; Y10T 436/101666; Y10S 435/971; Y10S 435/973

See application file for complete search history.

(56) References Cited

U.S. PATENT DOCUMENTS

| | | | |
|---|---|---|---|
| 5,635,363 | A | 6/1997 | Altman et al. |
| 5,693,539 | A | 12/1997 | Miltenyi et al. |
| 5,707,799 | A | 1/1998 | Hansmann et al. |
| 5,715,946 | A | 2/1998 | Reichenbach |
| 5,837,115 | A | 11/1998 | Austin et al. |
| 6,156,270 | A | 12/2000 | Buechler et al. |
| 6,190,870 | B1 | 2/2001 | Schmitz et al. |
| 6,471,860 | B1 | 10/2002 | Miltenyi et al. |
| 6,613,525 | B2 | 9/2003 | Nelson et al. |
| 6,645,731 | B2 | 11/2003 | Terstappen et al. |
| 6,685,841 | B2 | 2/2004 | Lopez et al. |
| 6,913,697 | B2 | 7/2005 | Lopez et al. |
| 7,030,228 | B1 | 4/2006 | Schmitz et al. |
| 7,150,812 | B2 | 12/2006 | Huang et al. |
| 7,166,423 | B1 | 1/2007 | Miltenyi et al. |
| 7,190,818 | B2 | 3/2007 | Ellis et al. |
| 7,262,269 | B2 | 8/2007 | Lam et al. |
| 7,428,325 | B2 | 9/2008 | Douglass et al. |
| 7,783,098 | B2 | 8/2010 | Douglass et al. |
| 7,785,810 | B2 | 8/2010 | Chen |
| 8,008,032 | B2 | 8/2011 | Forsyth et al. |
| 8,137,912 | B2 | 3/2012 | Kapur et al. |
| 8,354,075 | B1 | 1/2013 | Tai et al. |
| 9,174,222 | B2 | 11/2015 | Huang et al. |

(Continued)

FOREIGN PATENT DOCUMENTS

| | | |
|---|---|---|
| EP | 1597353 B1 | 11/2010 |
| WO | WO 2002/012896 A1 | 2/2002 |

(Continued)

OTHER PUBLICATIONS

Kurihara et al. Imaging Brain Tumors by Targeting Peptide Radiopharmaceuticals through Blood-Brain Barrier, Cancer Research 59: 6159-6163 (Dec. 15, 1999).*

(Continued)

*Primary Examiner* — Gailene Gabel

(74) *Attorney, Agent, or Firm* — Law Office of: Michael A. Sanzo, LLC

(57) ABSTRACT

Method of enriching specific cells from cellular samples are disclosed, comprising contacting in solution a cellular sample with affinity-tagged ligands (ATLs) each comprising a first ligand linked to an affinity tag, wherein the ligand selectively binds a cellular marker of the rare cells and the affinity tag can be selectively captured by a capture moiety, wherein the affinity tags do not comprise a magnetic particle; and flowing the sample through a microfluidic device comprising the capture moiety to selectively retain ATL-bound cells. Methods for enriching circulating tumor cells, and devices for enriching specific cells from cellular samples are also disclosed.

20 Claims, 8 Drawing Sheets

Specification includes a Sequence Listing.

(56) References Cited

U.S. PATENT DOCUMENTS

| | | | | |
|---|---|---|---|---|
| 2003/0159999 | A1 | 8/2003 | Oakey et al. | |
| 2004/0005582 | A1 | 1/2004 | Shipwash | |
| 2004/0018611 | A1 | 1/2004 | Ward et al. | |
| 2004/0048360 | A1 | 3/2004 | Wada et al. | |
| 2004/0144651 | A1 | 7/2004 | Huang et al. | |
| 2004/0229349 | A1 | 11/2004 | Daridon | |
| 2005/0266433 | A1 | 12/2005 | Kapur et al. | |
| 2005/0282220 | A1 | 12/2005 | Prober et al. | |
| 2006/0024756 | A1 | 2/2006 | Tibbe et al. | |
| 2006/0134599 | A1 | 6/2006 | Toner et al. | |
| 2006/0151265 | A1 | 7/2006 | Honjou et al. | |
| 2006/0223178 | A1 | 10/2006 | Kapur et al. | |
| 2006/0226433 | A1 | 10/2006 | Kawano | |
| 2006/0252054 | A1 | 11/2006 | Lin et al. | |
| 2006/0252087 | A1 | 11/2006 | Tang et al. | |
| 2006/0266692 | A1 | 11/2006 | Foster et al. | |
| 2006/0285996 | A1 | 12/2006 | Ohman et al. | |
| 2007/0020772 | A1 | 1/2007 | Cao et al. | |
| 2007/0026381 | A1 | 2/2007 | Huang et al. | |
| 2007/0026414 | A1 | 2/2007 | Fuchs et al. | |
| 2007/0059680 | A1 | 3/2007 | Kapur et al. | |
| 2007/0099207 | A1 | 5/2007 | Fuchs et al. | |
| 2007/0160503 | A1 | 7/2007 | Sethu et al. | |
| 2007/0196820 | A1 | 8/2007 | Kapur et al. | |
| 2007/0212737 | A1 | 9/2007 | Clarke et al. | |
| 2008/0090239 | A1 | 4/2008 | Shoemaker et al. | |
| 2008/0124721 | A1* | 5/2008 | Fuchs ................ | G01N 33/5091 435/6.12 |
| 2009/0136982 | A1 | 5/2009 | Tang et al. | |
| 2009/0215088 | A1 | 8/2009 | Forsyth et al. | |
| 2010/0055758 | A1 | 3/2010 | Kapur et al. | |
| 2010/0059414 | A1 | 3/2010 | Sturm et al. | |
| 2010/0167337 | A1 | 7/2010 | Tsinberg et al. | |
| 2010/0248358 | A1 | 9/2010 | Yoshioka | |
| 2011/0300603 | A1 | 12/2011 | Forsyth et al. | |
| 2012/0034628 | A1 | 2/2012 | Lesko et al. | |
| 2013/0260392 | A1 | 10/2013 | Forsyth et al. | |
| 2013/0302796 | A1 | 11/2013 | Fuchs et al. | |
| 2015/0260711 | A1 | 9/2015 | Toner et al. | |
| 2016/0002737 | A1 | 1/2016 | Fuchs et al. | |

FOREIGN PATENT DOCUMENTS

| | | | |
|---|---|---|---|
| WO | WO 2006/108087 | A2 | 10/2006 |
| WO | WO 2007/126938 | A2 | 11/2007 |
| WO | WO 2008/017871 | A1 | 2/2008 |
| WO | WO 2012/024194 | | 2/2012 |
| WO | WO 2012/094642 | | 7/2012 |
| WO | WO 2018/080997 | | 5/2018 |

OTHER PUBLICATIONS

Nagrath et al. Isolation of rare circulating tumour cells in cancer patients by microchip technology (Nature 450: (20/27): 1235-1238 (Dec. 2007).*

Aggarwal et al. A combinatorial approach to the selective capture of circulating malignant epithelial cells by peptide ligands, Biomaterials 26: 6077-6086 (2005).*

Aggarwal, et al. A combinatorial approach to the selective capture of circulating malignant epithelial cells by peptide ligands. Biomaterials. Oct. 2005;26(30):6077-86.

Fan, et al. Biotin derivatives of methotrexate and folate. Synthesis and utilization for affinity purification of two membrane-associated folate transporters from L1210 cells. J Biol Chem. Aug. 15, 1991;266(23):14862-5.

He, et al. In vivo quantitation of rare circulating tumor cells by multiphoton intravital flow cytometry. Proc Natl Acad Sci U S A. Jul. 10, 2007;104(28):11760-5.

Kurihara, et al. Imaging brain tumors by targeting peptide radiopharmaceuticals through the blood-brain barrier. Cancer Res. Dec. 15, 1999;59(24):6159-63.

Li, et al. Identification and characterization of a novel peptide ligand of epidermal growth factor receptor for targeted delivery of therapeutics. FASEB J. Dec. 2005;19(14):1978-85.

Nagrath, et al. Isolation of rare circulating tumour cells in cancer patients by microchip technology. Nature. 2007; 450: 1235-1241 (with Supplemental pp. 1-10).

Notice of allowance dated May 26, 2011 for U.S. Appl. No. 12/037,077.

Office action dated Oct. 27, 2010 for U.S. Appl. No. 12/037,077.

Sandoval, et al. Uptake and trafficking of fluorescent conjugates of folic acid in intact kidney determined using intravital two-photon microscopy. Am J Physiol Cell Physiol. Aug. 2004;287(2):C517-26.

Office action dated Jun. 1, 2012 for U.S. Appl. No. 13/182,003.

Office action dated Sep. 2, 2014 for U.S. Appl. No. 13/803,741.

Office action dated Sep. 13, 2013 for U.S. Appl. No. 13/692,710.

U.S. Appl. No. 14/774,260, filed Sep. 10, 2015, 2016/0139012 A1, May 19, 2016, D'Silva, et al.

U.S. Appl. No. 14/774,268, filed Sep. 10, 2015, 2016/0047735 A1, Feb. 18, 2016, Grisham, et al.

U.S. Appl. No. 14/941,957, filed Nov. 16, 2015, 2016/0168539 A1, Jun. 16, 2016, Civin, et al.

U.S. Appl. No. 15/478,405, filed Apr. 4, 2017, 2017/0333900 A1, Nov. 23, 2017, Grisham, et al.

U.S. Appl. No. 15/329,753, filed Jan. 27, 2017, 2017/0209864 A1, Jul. 27, 2017, Grisham, et al.

U.S. Appl. No. 15/204,693, filed Jul. 7, 2016, 2017/0101680 A1, Apr. 13, 2017, Kopf-Sill, et al.

U.S. Appl. No. 15/595,548, filed May 15, 2017, 2017/0248508 A1, Aug. 31, 2017, Ward, et al.

U.S. Appl. No. 16/108,365, filed Aug. 22, 2018, Not yet available, not available, Ward, et al.

U.S. Appl. No. 16/123,056, filed Sep. 6, 2018, Not yet available, not available, D'Silva, et al.

* cited by examiner

FIG. 3

| | |
|---|---|
| 2AR<br>A DISINTEGRIN<br>ACTIVATOR OF THYROID AND RETINOIC<br>ACID RECEPTOR (ACTR)<br>ADAM 11<br>ADIPOGENESIS INHIBITORY FACTOR (ADIF)<br>ALPHA 6 INTEGRIN SUBUNIT<br>ALPHA V INTEGRIN SUBUNIT<br>ALPHA-CATENIN<br>AMPLIFIED IN BREAST CANCER 1 (AIB1)<br>AMPLIFIED IN BREAST CANCER 3 (AIB3)<br>AMPLIFIED IN BREAST CANCER 4 (AIB4)<br>AMYLOID PRECURSOR PROTEIN SECRETASE<br>(APPS)<br>AP-2 GAMMA<br>APPS<br>ATP-BINDING CASSETTE<br>TRANSPORTER (ABCT) PLACENTA-SPECIFIC<br>(ABCP)<br>ATP-BINDING CASSETTE SUBFAMILY C<br>MEMBER (ABCC1)<br>BAG-1<br>BASIGIN (BSG)<br>BCEI<br>B-CELL DIFFERENTIATION FACTOR (BCDF)<br>B-CELL LEUKEMIA 2 (BCL-2)<br>B-CELL STIMULATORY FACTOR-2 (BSF-2)<br>BCL-1<br>BCL-2-ASSOCIATED X PROTEIN (BAX)<br>BCRP<br>BETA 1 INTEGRIN SUBUNIT<br>BETA 3 INTEGRIN SUBUNIT<br>DIFFERENTIATION-INHIBITING ACTIVITY<br>(DIA)<br>DNA AMPLIFIED IN MAMMARY CARCINOMA<br>1 (DAM1)<br>DNA TOPOISOMERASE II ALPHA<br>DR-NM23<br>E-CADHERIN<br>EMMPRIN<br>EMS1<br>ENDOTHELIAL CELL<br>GROWTH FACTOR (ECGR)<br>PLATELET-DERIVED (PD-ECGF)<br>ENKEPHALINASE<br>EPIDERMAL GROWTH FACTOR RECEPTOR<br>(EGFR)<br>BETA 5 INTEGRIN SUBUNIT<br>BETA-2 INTERFERON<br>BETA-CATENIN<br><br><br><br><br>BETA-CATENIN<br>BONE SIALOPROTEIN (BSP) | MMP17<br>MOESIN<br>MONOCYTE ARGININE-SERPIN<br>MONOCYTE-DERIVED NEUTROPHIL<br>CHEMOTACTIC FACTOR<br>MONOCYTE-DERIVED PLASMINOGEN<br>ACTIVATOR INHIBITOR<br>MTS-1<br>MUC-1<br>MUC18<br>MUCIN LIKE CANCER ASSOCIATED ANTIGEN<br>(MCA)<br>MUCIN<br>MUC-1<br>MULTIDRUG RESISTANCE PROTEIN 1 (MDR,<br>MDR1)<br>MULTIDRUG RESISTANCE RELATED PROTEIN-1<br>(MRP, MRP-1)<br>N-CADHERIN<br>GM-CSF<br>GRANULOCYTE CHEMOTACTIC PROTEIN 1<br>(GCP1)<br>GRANULOCYTE-MACROPHAGE-COLONY<br>STIMULATING FACTOR GROWTH FACTOR<br>RECEPTOR BOUND-7 (GRB-7)<br>GSTp<br>HAP<br>HEAT-SHOCK COGNATE PROTEIN 70 (HSC70)<br>HEAT-STABLE AssNTIGEN<br>HEPATOCYTE GROWTH FACTOR (HGF)<br>HEPATOCYTE GROWTH FACTOR RECEPTOR<br>(HGFR)<br>HEPATOCYTE-STIMULATING FACTOR III (HSF<br>III)<br>HER-2<br>HER2/NEU<br>HERMES ANTIGEN<br>HET<br>HHM<br>NEU<br>NEUTRAL ENDOPEPTIDASE<br>NEUTROPHIL-ACTIVATING PEPTIDE 1 (NAP1)<br>NM23-H1<br>NM23-H2<br>NME1<br>NME2<br>NUCLEAR RECEPTOR COACTIVATOR-1 (NCoA-1)<br>NUCLEAR RECEPTOR COACTIVATOR-2 (NCoA-2)<br>NUCLEAR RECEPTOR COACTIVATOR-3 (NCoA-3)<br>NUCLEOSIDE DIPHOSPHATE KINASE A (NDPKA)<br><br><br><br><br>NUCLEOSIDE DIPHOSPHATE KINASE B (NDPKB)<br>ONCOSTATIN M (OSM) |

FIG. 3 (Continued)

| | |
|---|---|
| BREAST CANCER ESTROGEN-INDUCIBLE SEQUENCE (BCEI) | ORNITHINE DECARBOXYLASE (ODC) |
| BREAST CANCER RESISTANCE PROTEIN (BCRP) | OSTEOCLAST DIFFERENTIATION FACTOR (ODF) |
| BREAST CANCER TYPE 1 (BRCA1) | OSTEOCLAST DIFFERENTIATION FACTOR RECEPTOR (ODFR) |
| BREAST CANCER TYPE 2 (BRCA2) | OSTEONECTIN (OSN, ON) |
| BREAST CARCINOMA AMPLIFIED SEQUENCE 2 (BCAS2) | OSTEOPONTIN (OPN) |
| CADHERIN EPITHELIAL CADHERIN-11 | OXYTOCIN RECEPTOR (OXTR) |
| CADHERIN-ASSOCIATED PROTEIN | p27/kipl |
| CALCITONIN RECEPTOR (CTR) | p300/CBP COINTEGRATOR ASSOCIATE PROTEIN (p/CIP) |
| CALCIUM PLACENTAL PROTEIN (CAPL) | p53 |
| CALCYCLIN | p9Ka |
| CALLA | PAI-1 |
| CAM5 | PAI-2 |
| CAPL | PARATHYROID ADENOMATOSIS 1 (PRAD1) |
| CARCINOEMBRYONIC ANTIGEN (CEA) | PARATHYROID HORMONE-LIKE HORMONE (PTHLH) |
| CATENIN ALPHA 1 | PARATHYROID HORMONE-RECEPTOR EXPRESSION-1 (ICERE-1) |
| CATHEPSIN B | KAI1 |
| CATHEPSIN D | KDR |
| CATHEPSIN K | KERATIN 8 |
| CATHEPSIN L2 | KERATIN 18 |
| CATHEPSIN O | KERATIN 19 |
| CATHEPSIN OI | KISS-1 |
| CATHEPSIN V | LEUKEMIA INHIBITORY FACTOR (LIF) |
| CD10 | LIF |
| CD146 | LOST IN INFLAMMATORY BREAST CANCER (LIBC) |
| CD147 | LOT ("LOST ON TRANSFORMATION") |
| CD24 | LYMPHOCYTE HOMING RECEPTOR |
| GAMMA-CATENIN | MACROPHAGE-COLONY STIMULATING FACTOR |
| GAP JUNCTION PROTEIN (26 kDa) | MAGE-3 |
| GAP JUNCTION PROTEIN (43 kDa) | MAMMAGLOBIN |
| GAP JUNCTION PROTEIN ALPHA-1 (GJA1) | MASPIN |
| GAP JUNCTION PROTEIN BETA-2 (GJB2) | MC56 |
| GCP1 | M-CSF |
| GELATINASE A | MDC |
| GELATINASE B | MDNCF |
| GELATINASE (72 kDa) | MDR |
| GELATINASE (92 kDa) | P-CADHERIN |
| GLIOSTATIN | PD-ECGF |
| GLUCOCORTICOID RECEPTOR INTERACTING PROTEIN 1 (GRIP1) | PDGF-β |
| GLUTATHIONE S-TRANSFERASE p | PEANUT-REACTIVE URINARY MUCIN (PUM) |
| CD29 | P-GLYCOPROTEIN (P-GP) |
| CD44 | PGP-1 |
| CD51 | PHGS-2 |
| CD54 | PHS-2 |
| CD61 | PIP |
| CD66e | PLAKOGLOBIN PLASMINOGEN ACTIVATOR INHIBITOR (TYPE 1) |
| CD82 | PLASMINOGEN ACTIVATOR INHIBITOR (TYPE 2) |
| CD87 | PLASMINOGEN ACTIVATOR (TISSUE-TYPE) |
| CD9 | |
| CEA | |

FIG. 3 (Continued)

| | |
|---|---|
| CELLULAR RETINOL-BINDING PROTEIN 1 (CRBP1) | PLASMINOGEN ACTIVATOR (UROKINASE-TYPE) |
| c-ERBB-2 | PLATELET GLYCOPROTEIN IIIa (GP3A) |
| CK7 | PLAU |
| CK8 | PLEOMORPHIC ADENOMA GENE-LIKE 1 (PLAGL1) |
| CK18 | POLYMORPHIC EPITHELIAL MUCIN (PEM) |
| CK19 | PRAD1 |
| CK20 | PROGESTERONE RECEPTOR (PgR) |
| CLAUDIN-7 | PROGESTERONE RESISTANCE |
| c-MET | PROSTAGLANDIN ENDOPEROXIDE SYNTHASE-2 |
| COLLAGENASE | PROSTAGLANDIN G/H SYNTHASE-2 |
| FIBROBLAST | PROSTAGLANDIN H SYNTHASE-2 |
| COLLAGENASE | pS2 |
| INTERSTITIAL | PS6K |
| COLLAGENASE-3 | PSORIASIN |
| COMMON ACUTE | PTHLH |
| LYMPHOCYTIC LEUKEMIA | PTHrP |
| ANTIGEN (CALLA) | RAD51 |
| CONNEXIN 26 (Cx26) | NEP |
| CONNEXIN 43 (Cx43) | RAD52 |
| CORTACTIN | RAD54 |
| COX-2 | RAP46 |
| CTLA-8 | RECEPTOR-ASSOCIATED COACTIVATOR 3 (RAC3) |
| CTR | REPRESSOR OF ESTROGEN RECEPTOR ACTIVITY (REA) |
| CTSD | S100A4 |
| CYCLIN D1 | S100A6 |
| CYCLOOXYGENASE-2 | S100A7 |
| CYTOKERATIN 18 | S6K |
| CYTOKERATIN 19 | SART-1 |
| CYTOKERATIN 8 | SCAFFOLD ATTACHMENT FACTOR B (SAF-B) |
| CYTOTOXIC T-LYMPHOCYTE-ASSOCIATED SERINE ESTERASE 8 (CTLA-8) | SCATTER FACTOR (SF) SECRETED PHOSPHOPROTEIN-1 (SPP-1) |
| HUMORAL | SECRETED PROTEIN ACIDIC AND RICH IN CYSTEINE (SPARC) |
| HYPERCALCEMIA OF MALIGNANCY (HHM) | STANNICALCIN |
| ICERE-1 | STEROID RECEPTOR COACTIVATOR-1 (SRC-1) |
| INT-1 | STEROID RECEPTOR COACTIVATOR-2 (SRC-2) |
| INTERCELLULAR ADHESION MOLECULE-1 (ICAM-1) | STEROID RECEPTOR COACTIVATOR-3 (SRC-3) |
| INTERFERON-GAMMA-INDUCING FACTOR (IGIF) | STEROID RECEPTOR RNA ACTIVATOR (SRA) |
| INTERLEUKIN-1 ALPHA (IL-1A) | STROMELYSIN-1 |
| INTERLEUKIN-1 BETA (IL-1B) | STROMELYSIN-3 |
| INTERLEUKIN-11 (IL-11) | TENASCIN-C (TN-C) |
| INTERLEUKIN-17 (IL-17) | TESTES-SPECIFIC PROTEASE 50 |
| INTERLEUKIN-18 (IL-18) | THROMBOSPONDIN I |
| INTERLEUKIN-6 (IL-6) | THROMBOSPONDIN II |
| INTERLEUKIN-8 (IL-8) | THYMIDINE PHOSPHORYLASE (TP) |
| INVERSELY CORRELATED WITH ESTROGEN | THYROID HORMONE RECEPTOR ACTIVATOR MOLECULE 1 (TRAM-1) |
| EPISIALIN | TIGHT JUNCTION PROTEIN 1 (TJP1) |
| EPITHELIAL MEMBRANE ANTIGEN (EMA) | TIMP1 |
| ER-ALPHA | TIMP2 |
| ERBB2 | |
| ERBB4 | |

FIG. 3 (Continued)

| | |
|---|---|
| ER-BETA<br>ERF-1<br>ERYTHROID-POTENTIATING ACTIVITY (EPA)<br>ESR1<br>ESTROGEN RECEPTOR-ALPHA<br>ESTROGEN RECEPTOR-BETA<br>ETS-1<br>EXTRACELLULAR MATRIX<br>METALLOPROTEINASE INDUCER (EMMPRIN)<br>FIBRONECTIN RECEPTOR BETA<br>POLYPEPTIDE (FNRB)<br>FIBRONECTIN RECEPTOR BETA SUBUNIT<br>(FNRB)<br>FLK-1<br>GA15.3<br>GA733.2<br>GALECTIN-3<br>MELANOMA CELL ADHESION MOLECULE<br>(MCAM)<br>MEMBRANE METALLOENDOPEPTIDASE<br>(MME)<br>MEMBRANE-ASSOCIATED<br>NEUTRAL ENDOPEPTIDASE (NEP)<br>CYSTEINE-RICH PROTEIN (MDC)<br>METASTASIN (MTS-1)<br>MLN64<br>MMP1<br>MMP2<br>MMP3<br>MMP7<br>MMP9<br>MMP11<br>MMP13<br>MMP14<br>MMP15<br>MMP16 | TIMP3 RELATED PEPTIDE (PTHrP)<br>TIMP4<br>TISSUE-TYPE PLASMINOGEN ACTIVATOR<br>TN-C<br>TP53<br>tPA<br>TRANSCRIPTIONAL INTERMEDIARY FACTOR 2<br>(TIF2)<br>TREFOIL FACTOR 1 (TFF1)<br>TSG101<br>TSP-1<br>TSP1<br>TSP-2<br>TSP2<br>TSP50<br>TUMOR CELL COLLAGENASE STIMULATING<br>FACTOR (TCSF)<br>TUMOR-ASSOCIATED EPITHELIAL MUCIN<br>uPA<br>uPAR<br>UROKINASE<br>UROKINASE-TYPE PLASMINOGEN ACTIVATOR<br>UROKINASE-TYPE PLASMINOGEN ACTIVATOR<br>RECEPTOR (uPAR)<br>UVOMORULIN<br>VASCULAR ENDOTHELIAL GROWTH FACTOR<br>VASCULAR ENDOTHELIAL GROWTH FACTOR<br>RECEPTOR-2 (VEGFR2)<br>VASCULAR ENDOTHELIAL GROWTH FACTOR-A<br>VASCULAR PERMEABILITY FACTOR<br>VEGFR2<br>VERY LATE T-CELL ANTIGEN BETA (VLA-BETA)<br>VIMENTIN<br>VITRONECTIN RECEPTOR ALPHA POLYPEPTIDE<br>(VNRA)<br>VITRONECTIN RECEPTOR<br>VON WILLEBRAND FACTOR<br>VPF<br>VWF<br>WNT-1<br>ZAC<br>ZO-1<br>ZONULA OCCLUDENS-1 |

TAGGED LIGANDS FOR ENRICHMENT OF RARE ANALYTES FROM A MIXED SAMPLE

CROSS-REFERENCE

This application is a continuation of U.S. application Ser. No. 14/103,352, filed Dec. 11, 2013 which is a continuation of U.S. application Ser. No. 13/692,710, filed Dec. 3, 2012, now abandoned, which is a continuation of U.S. application Ser. No. 13/182,003, filed Jul. 13, 2011, now abandoned, which is a divisional of U.S. application Ser. No. 12/037,077, now U.S. Pat. No. 8,008,032, filed Feb. 25, 2008, which applications are incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 11, 2014, is named 32061-721-302-Seqlist.txt and is 22,363 bytes in size.

BACKGROUND OF THE INVENTION

Analysis of a complex mixture such as blood can be difficult but provides valuable information. For example, CD4 T cell levels can reflect the course of disease in AIDS patients, cellular lymphoid and myeloid markers can aid leukemia and lymphoma diagnoses, and the presence of errant epithelial cells in the blood may signify a metastasizing cancer.

Such complex mixtures can be analyzed by fluorescent activated cell sorting (FACS), a technology that can quantitate marked analytes and also separate them out from the mixtures. Another popular method of cell separation involves magnetically labeling a target population of cells, e.g. with ferromagnetic beads, followed by sorting the labeled cells by passing them through a receptacle positioned within a magnetic field, a process also known as magnetic activated cell sorting (MACS). Despite their widespread use, FACS and MACS technologies have disadvantages, for example, they require machinery that is expensive and difficult to maintain. FACS technology has the added disadvantage of having limited portability.

Given the heavy demand, new approaches and technologies for cell sorting are needed for medical diagnostics and other applications.

SUMMARY OF THE INVENTION

In one aspect, methods for enriching specific cells in a cellular sample are provided. The methods comprise a method for enriching rare cells from a cellular sample comprising contacting in solution a cellular sample with affinity-tagged ligands (ATLs) each comprising a first ligand linked to an affinity tag, wherein the ligand selectively binds a cellular marker of the rare cells and the affinity tag can be selectively captured by a capture moiety, wherein the affinity tags do not comprise a magnetic particle; and flowing the sample through a microfluidic device comprising the capture moiety to selectively retain ATL-bound cells.

In some embodiments, the method comprises a method for enriching rare cells from a cellular sample comprising: contacting in solution the cellular sample with affinity-tagged ligands (ATLs) each comprising:

a ligand linked to a plurality of affinity tags, wherein the ligand selectively binds a cellular marker of the rare cells and the affinity tag can be selectively captured by a capture moiety and wherein the ratio of ligand:affinity tag of the ATL's is less than 1:1; flowing the sample through a microfluidic device comprising the capture moiety to selectively retain ATL-bound cells.

In one aspect, methods for enriching specific cells in a cellular sample are provided. The methods comprise a method for enriching rare cells, wherein the rare cells are circulating tumor cells or epithelial cells, from a cellular sample comprising contacting in solution a cellular sample with affinity-tagged ligands (ATLs) each comprising a first ligand linked to an affinity tag, wherein the ligand is folic acid, *Dolichos Biflorus* Agglutinin (DBAs), epidermal growth factor (EGF), EGF peptide (amino acid sequence YHWYGYTPQNVI, SEQ ID NO:1), epi peptide (amino acid sequence QMARIPKRLARH, SEQ ID NO:2), transforming growth factor-alpha (TGF-alpha), Urokinase Plasminogen Activator (UPA), FasL, MUC1/sec, catenin, ICAM-1, plasminogen, or the like and selectively binds a cellular marker of the rare cells and the affinity tag can be selectively captured by a capture moiety, wherein the affinity tags comprise biotin, desthiobiotin, histidine, polyhistidine, myc, hemagglutinin (HA), FLAG, fluorescence tag, tandem affinity purification (TAP) tags, FLAG, or glutathione S transferase (GST) or derivatives thereof; and flowing the sample through a microfluidic device comprising the capture moiety to selectively retain ATL-bound cells; wherein the capture moiety comprises avidin, streptavidin, Neutravidin™, nickel, or glutathione or other molecule capable of binding the affinity tag; and wherein the cellular marker is a cancer marker for one or more of breast, prostate, liver, ovary, skin, colon, rectum, cervix, esophagus, stomach, brain, lung, or endometrium cancer.

In some embodiments, the method comprises a method for enriching rare cells from a cellular sample comprising: contacting in solution the cellular sample with affinity-tagged ligands (ATLs) each comprising:

a ligand linked to a plurality of affinity tags, wherein the ligand is folic acid or epidermal growth factor (EGF) and. selectively binds a cellular marker of the rare cells wherein the rare cells are circulating tumor cells or epithelial cells, and the affinity tag and wherein the ratio of ligand:affinity tag of the ATL's is less than 1:1; flowing the sample through a microfluidic device comprising the capture moiety to selectively retain ATL-bound cells.

In one aspect, methods for enriching specific cells in a cellular sample are provided. The methods comprise a method for enriching rare cells, wherein the rare cells are circulating tumor cells or epithelial cells, from a cellular sample comprising contacting in solution a cellular sample with affinity-tagged ligands (ATLs) each comprising a first ligand linked to an affinity tag, wherein the ligand is an antibody that is anti-EpCam; anti-E-Cadherin, anti-Mucin-1, anti-Cytokeratin (CK) 8, anti-epidermal growth factor receptor (EGFR), anti-cytokeratin (CK)19, anti-ErbB2, anti-PDGF, anti-L6, or anti-leukocyte associated receptor (LAR) and selectively binds a cellular marker of the rare cells and the affinity tag can be selectively captured by a capture moiety, wherein the affinity tags comprise biotin, desthiobiotin, histidine, polyhistidine, myc, hemagglutinin (HA), FLAG, fluorescence tag, tandem affinity purification (TAP) tags, FLAG, or glutathione S transferase (GST) or derivatives thereof; and flowing the sample through a microfluidic device comprising the capture moiety to selectively retain ATL-bound cells; wherein the capture moiety comprises avidin, streptavidin, Neutravidin™, nickel, or glutathione or other molecule capable of binding the affinity tag; and wherein the cellular marker is a cancer marker for one or more of breast, prostate, liver, ovary, skin, colon, rectum, cervix, esophagus, stomach, brain, lung, or endometrium cancer.

In some embodiments, the method comprises a method for enriching rare cells from a cellular sample comprising: contacting in solution the cellular sample with affinity-tagged ligands (ATLs) each comprising:

a ligand linked to a plurality of affinity tags, wherein the ligand is an antibody that is anti-EpCam; anti-E-Cadherin, anti-Mucin-1, anti-Cytokeratin (CK) 8, anti-epidermal growth factor receptor (EGFR), anti-cytokeratin (CK)19, anti-ErbB2, anti-PDGF, anti-L6, or anti-leukocyte associated receptor (LAR) and. selectively binds a cellular marker of the rare cells wherein the rare cells are circulating tumor cells or epithelial cells, and the affinity tag and wherein the ratio of ligand:affinity tag of the ATL's is less than 1:1; flowing the sample through a microfluidic device comprising the capture moiety to selectively retain ATL-bound cells.

In some embodiments, the method comprises a method for enriching rare analytes from a sample comprising:

contacting in solution said sample with a plurality of affinity-tagged ligands (ATLs) wherein said mixture of ATL's comprises: a first ATL comprising a first ligand that selectively binds a first marker of rare analytes, wherein the first ligand is linked to a first affinity tag that is selectively captured by a first capture moiety; and a second ATL comprising a second ligand that selectively binds a second marker of rare analytes, wherein said second ligand is linked to a second affinity tag, wherein the second affinity tag is selectively captured by the first capture moiety; and contacting the sample with the capture moiety to selectively enrich the rare analytes.

In some embodiments, the method comprises a method for enriching rare analytes from a sample comprising contacting in solution said sample with a plurality of affinity-tagged ligands (ATLs) wherein said mixture of ATL's comprises: a first ATL comprising a first ligand that selectively binds a first marker of rare analytes, wherein the first ligand is linked to a first affinity tag that is selectively captured by a first capture moiety; and a second ATL comprising a second ligand that selectively binds a second marker of rare analytes, wherein said second ligand is linked to a second affinity tag, wherein the second affinity tag is selectively captured by the first capture moiety; contacting the sample with the capture moiety to selectively enrich the rare analytes; wherein the first affinity tag and said second affinity tag are identical; and wherein the ligand is folic acid, (DBA), EGF; EGF peptide (amino acid sequence YHWYGYTPQNVI, SEQ ID NO:1), epi peptide (amino acid sequence QMARIPKRLARH, SEQ ID NO:2), TGF-alpha; Urokinase Plasminogen Activator (UPA), FasL, MUC1/sec, catenin, ICAM-1, plasminogen, or the like, or wherein the ligand is an antibody that is anti-EpCam; anti-E-Cadherin, anti-Mucin-1, anti-Cytokeratin (CK) 8, anti-epidermal growth factor receptor (EGFR), anti-cytokeratin (CK)19, anti-ErbB2, anti-PDGF, anti-L6, or anti-leukocyte associated receptor (LAR).

In some embodiments, the method comprises a method for enriching rare analytes such as cells from a sample such as a blood sample comprising: contacting in solution said sample with a plurality of affinity-tagged ligands (ATLs) wherein said mixture of ATL's comprises: a first ATL comprising a first ligand that selectively binds a first marker of rare analytes, wherein the first ligand is linked to a first affinity tag that is selectively captured by a first capture moiety; and a second ATL comprising a second ligand that selectively binds a second marker of rare analytes, wherein said second ligand is linked to a second affinity tag, wherein the second affinity tag is selectively captured by the first capture moiety; contacting the sample with the capture moiety to selectively enrich the rare analytes; wherein the mixture of ATL's comprises at least 3, 4, 5, 6, 7, 8, 9, or 10 ATL's each of which comprises an affinity tag that can be selectively captured by the first capture moiety;

In some embodiments, the method comprises a method for enriching rare analytes such as cells from a sample such as a blood sample comprising: contacting in solution said sample with a plurality of affinity-tagged ligands (ATLs) wherein said mixture of ATL's comprises: a first ATL comprising a first ligand that selectively binds a first marker of rare analytes, wherein the first ligand is linked to a first affinity tag that is selectively captured by a first capture moiety; and a second ATL comprising a second ligand that selectively binds a second marker of rare analytes, wherein said second ligand is linked to a second affinity tag, wherein the second affinity tag is selectively captured by the first capture moiety; contacting the sample with the capture moiety to selectively enrich the rare analytes; wherein the mixture of ATL's comprises at least 1, 2, 3, 4, 5, 6, 7, 8, 9, or 10 ATL's each of which comprises an affinity tag that can be selectively captured by the first capture moiety and wherein each of the ATL's comprises a ratio of Ligand: Affinity Tag that is less than 1:5; and wherein the capture moiety is in a microfluidic device such as a microfluidic device comprising an array of obstacles; wherein the first or second ligand is folic acid, (DBA), EGF; EGF peptide (amino acid sequence YHWYGYTPQNVI, SEQ ID NO:1), epi peptide (amino acid sequence QMARIPKRLARH, SEQ ID NO:2), TGF-alpha; Urokinase Plasminogen Activator (UPA), FasL, MUC1/sec, catenin, ICAM-1, plasminogen, or the like, or wherein the ligand is an antibody that is anti-EpCam; anti-E-Cadherin, anti-Mucin-1, anti-Cytokeratin (CK) 8, anti-epidermal growth factor receptor (EGFR), anti-cytokeratin (CK)19, anti-ErbB2, anti-PDGF, anti-L6, or anti-leukocyte associated receptor (LAR); and wherein the affinity tag comprises biotin, desthiobiotin, histidine, polyhistidine, myc, hemagglutinin (HA), FLAG, fluorescence tag, tandem affinity purification (TAP) tags, FLAG, or glutathione S transferase (GST) or derivatives thereof; wherein the ligand is linked to the affinity tag either directly or via a linker comprising modified dextran, polyethylene glycol, polypropylene glycol, polyvinyl alcohol, or polyvinylpyrrolidone; and wherein the capture moiety comprises avidin, streptavidin, Neutravidin™ nickel, or glutathione or other molecule capable of binding the affinity tag.

In some embodiments, the method comprises a method of diagnosing a condition such as cancer in a patient comprising: enriching rare cells from the patient through any of the methods described herein; and evaluating, identifying, or quantitating the ATL bound cells.

In some embodiments, the invention comprises a reagent comprising a plurality of affinity tagged ligands each of which comprises a ligand that selectively binds a different cancer cellular marker linked to an identical affinity tag that is selectively captured by a capture moiety wherein the ratio of ligand:affinity tag per ATL is less than 1:1; wherein the reagent comprises at least 1, 2, 3, 4, or 5 different ATL's.

In some embodiments, the device comprises a microfluidic device comprising an array of obstacles, wherein the obstacles are functionalized with capture moieties comprising EGF-peptide, EPI-peptide, folate or DBA.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

FIG. 3 is a Table of exemplary markers contemplated herein.

DETAILED DESCRIPTION OF THE INVENTION

Figure 1A:
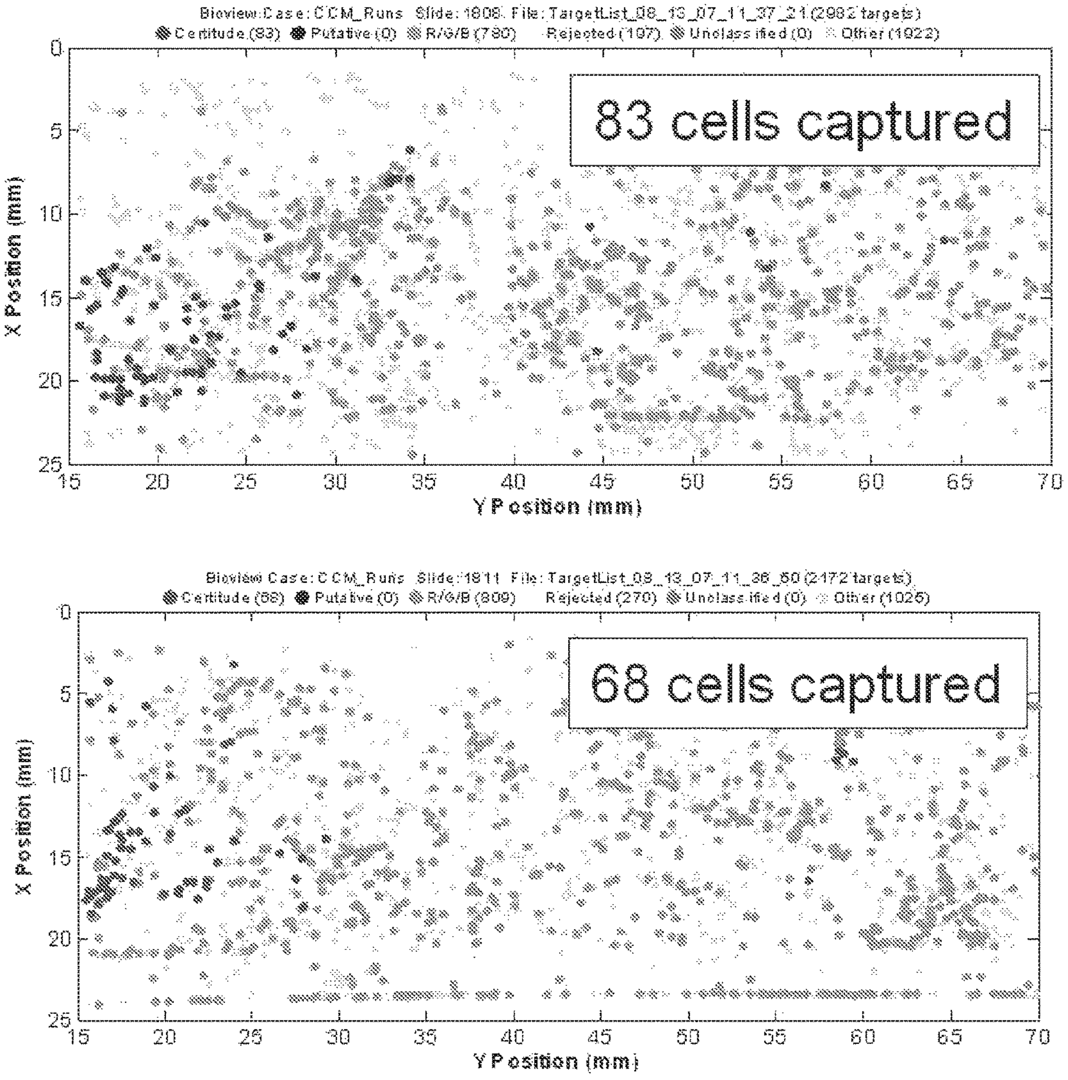
FIG. 1A depicts two fluorescent images illustrating the capture of lung cancer cells with a non-specific affinity tagged ligand (biotinylated anti-IgG).

The present disclosure provides compositions, methods and devices for the detection and isolation of rare analytes from a mixed sample. Rare analytes include cells and particles, such as eukaryotic cells, prokaryotic cells, cellular organelles, cellular fragments, viruses, nucleic acids, proteins, and protein complexes. A mixed sample may include a fluid sample, e.g., water, air, bodily fluids such as blood, urine, etc. A mixed sample may also include a solid sample that is liquefied, e.g., a tumor biopsy, food solids, etc.

Enrichment, detection, and isolation of rare analytes is accomplished using affinity-tagged ligands (ATLs). An ATL may comprise Formula I:

$$L_x\text{-}AT_n, \quad \text{(Formula I)}$$

wherein:

L is a ligand that selectively binds a marker for a rare analyte;

x is the number of ligands within each ATL;

AT is an affinity tag which can be selectively captured using a capture moiety; and n is the number of ATs linked to the ligand.

L and AT may be linked together directly or indirectly (via a linker). Linkers may be straight or branched. A linker may be a peptide, polypeptide, protein, and the like. In some embodiments, the linker moiety is a branched polymer. Such branched polymers include modified dextran, polyethylene glycol, polypropylene glycol, polyvinyl alcohol, polyvinylpyrrolidone, polyethylene acrylamide and combinations thereof. In some embodiments, the linker is branched and comprises multiple ATs. For example, in some embodiments an ATL comprises at least 5, 10, 15, 20, 25, 30, 35, 40, 50, 60, 70, 80, 90, 100 or more ATs per L. When a single ligand is linked to multiple AT's, the AT's can each be linked to the ligand via a single linker or via a plurality of linkers (e.g., one linker per AT).

Examples of ligands contemplated in the methods herein include ligands that selectively bind cell surface marker(s) (e.g., receptors and adhesion molecules) of rare cells of interest. A ligand can comprise molecule(s), peptide(s), polypeptides, particles, and the like, and/or fragments thereof. The ligand can be naturally occurring or artificially synthesized. Rare cells include circulating tumor cells (CTCs), circulating epithelial cells or circulating stem cells.

In some embodiments, a ligand comprises an antibody, such as a monoclonal antibody or a polyclonal antibody. Examples of ligand antibodies contemplated herein include antibodies that selectively bind CTCs, circulating epithelial cells, or circulating stem cells. In some embodiments, such antibodies selectively bind an antigen such as EpCam; E-Cadherin, Mucin-1, Cytokeratin (CK) 8, epidermal growth factor receptor (EGFR), cytokeratin (CK)19, ErbB2, PDGF, L6, or leukocyte associated receptor (LAR). In certain embodiments, the ligand may be an antibody to a marker listed in FIG. 3.

In other embodiments, a ligand is not an antibody. Examples of non-antibody ligands include folic acid, *Dolichos Biflorus* Agglutinin (DBA), epidermal growth factor (EGF), EGF peptide (amino acid sequence YHWYGYT-PQNVI, SEQ ID NO:1), epi peptide (amino acid sequence QMARIPKRLARH, SEQ ID NO:2), transforming growth factor-alpha (TGF-alpha), Urokinase Plasminogen Activator (UPA), FasL, MUC1/sec, catenin, ICAM-1, plasminogen, or the like. In some embodiments, the ligand activates a cellular process, and in other embodiments, the ligand may not activate a cellular process.

An ATL may have a single ligand or multiple ligands (e.g., $x>1$, or $x>2$, 5, 10, 20, or more). When an ATL comprises multiple ligands, each ligand may be identical to the other ligands, different from the other ligands, or a combination thereof.

Affinity tags (AT) can include molecules, peptides, polypeptides, particles, and/or other substances capable of being captured by a capture moiety or enrichment device. Examples of ATs include biotin, desthiobiotin, histidine, poly-histidine, glutathione S transferase (GST), myc, hemagglutinin (HA), FLAG, fluorescence tag, tandem affinity purification (TAP) tags, or derivatives thereof. The TAP tag may comprise calmodulin-binding protein, TEV, and protein A or G subunit. In some embodiments, the affinity tag comprises a magnetic particle. In other embodiments, the affinity tag is a molecule or particle other than a magnetic particle. In some instances, an affinity tag does not comprise an antibody.

As described above, an ATL may comprise one AT, or, for example, may comprise at least 2, 5, 10, 20, 30, 40, 50, 60, 70, 80, 90, 100, or more ATs.

To detect rare analytes (or single analyte) in a fluid sample, the sample is mixed with a homogenous or heterogeneous set of ATLs. The sample is incubated with the ATLs for a sufficient amount of time to enable binding of the ligands to the receptors or rare analytes. The sample and ATLs are then applied to one or more capture moieties that selectively bind the affinity tags, thereby allowing enrichment of the bound rare analytes. The capture moiety can be coupled to a solid support (e.g. a tube, a flat substrate, or an array of obstacles).

To detect rare analytes in a solid or semi-solid sample, the sample is first solubilized and then mixed with the mixture of ATLs as described above. Once the sample is incubated with the ATLs for a sufficient period of time to allow binding between the ligands and the rare analyte markers, the sample is applied to one or more capture moieties that selectively binds to the affinity tag.

Capture moieties may be inorganic molecules, organic molecules, peptides, polypeptides, and/or antibodies, and the like, or may include fragments of, or derivatives, of same. The capture moieties are capable of binding to, or interacting with, an affinity tag. Examples of capture moieties include, but are not limited to, a magnet or magnetized substrate, avidin, streptavidin, Neutravidin™, glutathione, nickel, calcium/calmodulin, or IgG. Other examples of capture moieties include magnetic or magnetized surfaces, avidin and avidin-coated particles.

In some instances, capture moieties are part of a microfluidic device (e.g., a microfluidic gap or channel coated with capture moieties). A microfluidic device contemplated herein can comprise an array of obstacles that form a network of microfluidic channels.

The affinity tags can bind irreversibly or reversibly to the capture moiety(ies). In some instances, an affinity tag may be releasable from the capture moiety. For example, desthiobiotin may be used as an affinity tag with avidin as the capture moiety. The bond between biotin and avidin can then be released by applying desphio-biotin or biotin to the sample.

In one example, the ATL's herein can be used to enrich rare analytes such as cells from a mixed sample such as blood. Such method comprises the step of contacting in solution a test sample with affinity-tagged ligands (ATLs). Each ATL comprises: at least one ligand linked to at least one affinity tag. The ligand and affinity tag are optionally liked via a linker comprising one or more of modified dextran, polyethylene glycol, polypropylene glycol, polyvinyl alcohol, or polyvinylpyrrolidone.

The ligands of the ATL's selectively bind a one or more markers of the rare analytes. The affinity tags of the ATLs are ones that can be selectively captured by a single capture moiety or a plurality of capture moieties. Examples of capture moieties contemplated for any of the embodiments herein include avidin, streptavidin, Neutravidin™, nickel, or glutathione. The affinity tags may be one that does not comprise a magnetic particle. Examples of affinity tags include biotin, desthiobiotin, histidine, polyhistidine, myc, hemagglutinin (HA), FLAG, fluorescence tag, tandem affinity purification (TAP) tags, FLAG, glutathione S transferase (GST) or derivatives thereof. After incubation for a sufficient amount of time to allow the sample and ATL's to mix, the mixed sample is contacted with one or more capture moieties or is flowed through a microfluidic device comprising the one or more capture moieties. This selectively retains ATL-bound analytes or cells.

In some instances, each ATL comprises a ratio of ligand to affinity tag such that there are more affinity tags for each ligand. In some instances the ligand:affinity tag ratio is less than 1:1 or less than 1:5 or less than 1:10 or less than 1:100. Furthermore, a single ATL can have at least 2, 3, 4, 5, 6, 7, 8, 9 or 10 different ligands. Each of the ligands can be specific to a different marker, such as a cancer marker.

Cellular cancer markers contemplated herein include markers for a cancer such as breast, prostate, liver, ovary, skin, colon, rectum, cervix, esophagus, stomach, brain, lung, pancreatic, or endometrium cancer. In some instances a cellular marker is epidermal growth factor receptor (EGFR), EPCAM, or folic acid receptor. In some instances, the cellular marker is E-Cadherin, Mucin-1, Cytokeratin (CK) 8, cytokeratin (CK)19, ErbB2, PDGF, L6, or leukocyte associated receptor (LAR) In other instances it is any marker listed in the table of FIG. 3.

To enrich rare analytes such as rare cells (epithelial cells or CTC) found in bodily fluid (e.g., blood), the ligands in the ATL's can be one or more of the following: folic acid, epidermal growth factor (EGF), transforming growth factor-alpha (TGF-alpha), Urokinase Plasminogen Activator (UPA), FasL, MUC1/sec, catenin, ICAM-1, plasminogen, or fragments thereof. In some embodiments, the ligands comprise haptens. In some instances, the ligand is an antibody and in others it is not an antibody.

In some instances, a reagent used to enrich/detect rare analytes comprises a plurality of affinity-tagged ligands (ATLs) wherein each ATL comprises: a first ATL comprising a first ligand that selectively binds a first marker of the rare analytes linked to a first affinity tag that is selectively captured by a first capture moiety; and a second ATL comprising a second ligand that selectively binds a second marker linked to a second affinity tag, wherein the second affinity tag is selectively captured by the first capture moiety. In such embodiments, the reagent described above is mixed with a mixed sample of analytes. After allowing the ATL's and sample to mix for a sufficient amount of time for binding to occur, the sample/ATL mixture is contacted with the first capture moiety to selectively enrich the rare analytes. The capture moiety can be avidin and the capture moiety can be in a microfluidic gap or channel. The first and second affinity tags can be identical (both biotin) or different (biotin and desphio-biotin) but both selectively captured by the same capture moiety. In some instances, a mixed sample such as the one described above is contacted with at least 3, 4, 5, 6, 7, 8, 9, or 10 different ATL's each of which comprises an affinity tag that can be selectively captured by a single capture moiety or the same affinity tag.

A sample, such as a blood sample, can be mixed with one or more different ATLs. In certain embodiments, ATLs of similar configuration may be contacted with the targeted analytes. In other embodiments, a mixture of different ATLs may be used. In still other embodiments, step-wise purification of the analyte may occur through sequential use of the same or different ATLs.

An exemplary ATL can have a single ligand comprising anti-EpCAM antibody linked to a plurality of ATs, each of which comprises a biotin molecule. The ATs are linked to the ligand via a branched linker such that each ligand is coupled to at least five ATs. In some embodiments, the ligand may bind the marker (EpCAM) at more than one site. In other embodiments, e.g., EGF, the ligand binds the marker only once. Once the sample is mixed with the ATLs, the sample flows through a microfluidic device, optionally comprising an array of obstacles, coated with avidin capture moieties. Enriched rare cells (e.g., circulating epithelial cells) can then be visualized/detected using any means known in the art, including fluorescent in situ hybridization (FISH) staining.

Some applications may require analysis downstream of the capture of the ATL-bound cells. In some embodiments, the ATLs may be conjugated to one or more detectable labels. Such detectable labels comprise fluorescent markers, HRP-alkaline phosphatase detection or quantum dots. In some embodiments, in addition to an ATL, the cells may be contacted with a detectably-labeled ligand specific for a cellular marker. Such detectable labels may comprise one or more of fluorescent probes, magnetic particles, or quantum dots. The detectably-labeled ligands comprise the ligands described herein relating to ATLs. An example of a detectably-labeled ligand is a fluorescently-labeled antibody.

Varying the number of affinity tags and/or ligands in a single ATL may affect the ability to capture target analytes. Thus, the disclosure provides ATLs with more than one affinity tag and/or more than one ligand. The affinity tags may be identical tags, similar tags, or different tags. Since higher affinity-tag-to-ligand ratios may result in enhanced or more efficient capture of cells, the ratio of affinity tag to ligand in a single ATL may be greater than or equal to 1, for example, 2:1, 3:1, 4:1, 5:1, 10:1, 20:1, or greater.

In some embodiments, the marker is a marker for one or more of the following: cancer of the breast, lung, prostate, liver, ovary, skin, colon, rectum, cervix, esophagus, stomach, brain, bladder, kidney, testicular, or endometrium. In some embodiments, the marker is for a blood cancer such as leukemia or lymphoma.

In some embodiments, vascular disease is monitored by enriching for cells with endothelial markers. Other cancers may also be monitored by enriching for endothelial cells. In some embodiments, fetal markers (e.g. Y chromosome proteins, gamma globin) are used for capturing fetal cells in the maternal circulation. In some embodiments, stem cell markers (CD44) are used to capture stem cells.

In certain embodiments, the methods provided comprise contacting a cellular sample with one or more ATLs to enable binding to one or more cellular markers, followed by capture of the bound cells by an enrichment device. The contacting of the cellular sample with one or more ATLs may occur under conditions pre-determined to maximize binding efficiency. In some embodiments, the conditions may be optimized to minimize non-specific binding. For example, the timing of the contacting between the cellular sample and the one or more ATLs may be optimized. Such optimized or predetermined amount of time may be used for the contacting step. Likewise, conditions for the temperature of the contacting step may be optimized to maximize binding efficiency and/or to minimize internalization of cellular markers. A pre-determined or optimized temperature or temperatures may be used for the contacting step. In some embodiments, the composition of the solution containing the cellular sample and/or the ATL may be optimized for more efficient binding. Blocking reagents or serums may be added to aid in binding efficiency. Examples of such blocking reagents include bovine serum albumin (BSA), fetal calf serum (FCS), milk, and other commercially-obtainable reagents.

The methods may further comprise a wash step in which unbound (or free) ATL is removed from the cellular sample prior to capture by the enrichment device. For example, the wash step could be accomplished by one or more rounds comprising centrifugation of the cellular sample, aspiration of the supernatant, and re-suspension of the cellular sample in wash buffer. The composition of the wash buffer may comprise buffered solutions and may be optimized to maximize binding efficiency. The optimized wash buffer may comprise one or more blocking reagents or serums described herein.

In some embodiments, the cells are added to an enrichment device that comprises a surface functionalized with a capture moiety recognizing the affinity tag or a cellular marker, such as a receptor. In certain embodiments, a surface of the enrichment device is coated or treated with one or more capture moieties (e.g., avidin or Neutravidin) in order to allow capture of the ATL-bound cells. In certain embodiments, such capture-moieties are not antibodies. In some embodiments, such capture moieties are ligands. In some embodiments, the enrichment device comprises a surface coated or functionalized with a ligand that is used to directly enrich cells expressing a specific marker from a mixed cell population. In some embodiments, the surface of such enrichment device is functionalized with folate in order to enrich cells expressing the folate receptor. In some embodiments, the enrichment device is functionalized with *Dolichos Biflorus* Agglutinin (DBA), epidermal growth factor (EGF), EGF peptide (amino acid sequence YHWYGYTPQNVI, SEQ ID NO:1), epi peptide (amino acid sequence QMARIPKRLARH, SEQ ID NO:2), transforming growth factor-alpha (TGF-alpha), Urokinase Plasminogen Activator (UPA), FasL, MUC1/sec, catenin, ICAM-1, plasminogen, or the like. Parameters such as timing, temperature, and/or buffer composition may be optimized to promote optimal capture by the enrichment device.

The enrichment device may include one or more arrays of obstacles that allow lateral displacement of cells and other components of fluids. Such arrays of obstacles comprise different configurations. In one configuration, a row or rows of obstacles are arranged with a 50% offset from other randomly- or non-randomly-arranged obstacles creating restricted and expanded gaps.

In some embodiments, the obstacles within the array of obstacles are coated or treated with one or more capture moieties or ligands. In some embodiments, the enrichment device is capable of sorting cells based on another variable, e.g. hydrodynamic size, as well as capturing ATL-bound cells. Enrichment devices include, but are not limited to centrifuge, microfuge and ultracentrifuge test tubes. In some embodiments, the enrichment device is a column or other such receptacle such as a magnetic activated cell sorting (MACS) column.

Any of the ATLs herein may be designed to enrich cancer cells as well as prognose and diagnose cancer conditions. For example, cancer can be staged or diagnosed by enriching rare cells (e.g., epithelial cells, circulating cancer stem cells) using ATL's by any of the means described above. Subsequently, the enriched cells can be further evaluated or quantified. In one instance, diagnosis or prognoses comprises comparing the percentage or quantity of epithelial cells in the blood of a test subject with that in the blood of a healthy control subject, a panel of healthy control subjects, known standard levels, or similar information obtained from the same patient at a different point in time.

Peptide Library

In some embodiments, the present disclosure provides a method for screening a combinatorial peptide library for peptide ligands capable of binding cell surface markers. Such methods comprise contacting a sample of cancer cells with a combinatorial peptide library, wherein the peptides have been pre-labeled with one or more affinity tags, described herein; purifying out the cells selectively binding to candidate peptide ligands; and identifying the candidate ligands bound to the cells. In certain embodiments, the purifying may comprise the lateral flow of the cellular sample through a device coated with capture moieties that selectively bind the ATs so as to permit capture of the ATL bound cells.

EXAMPLES

Figure 1B:
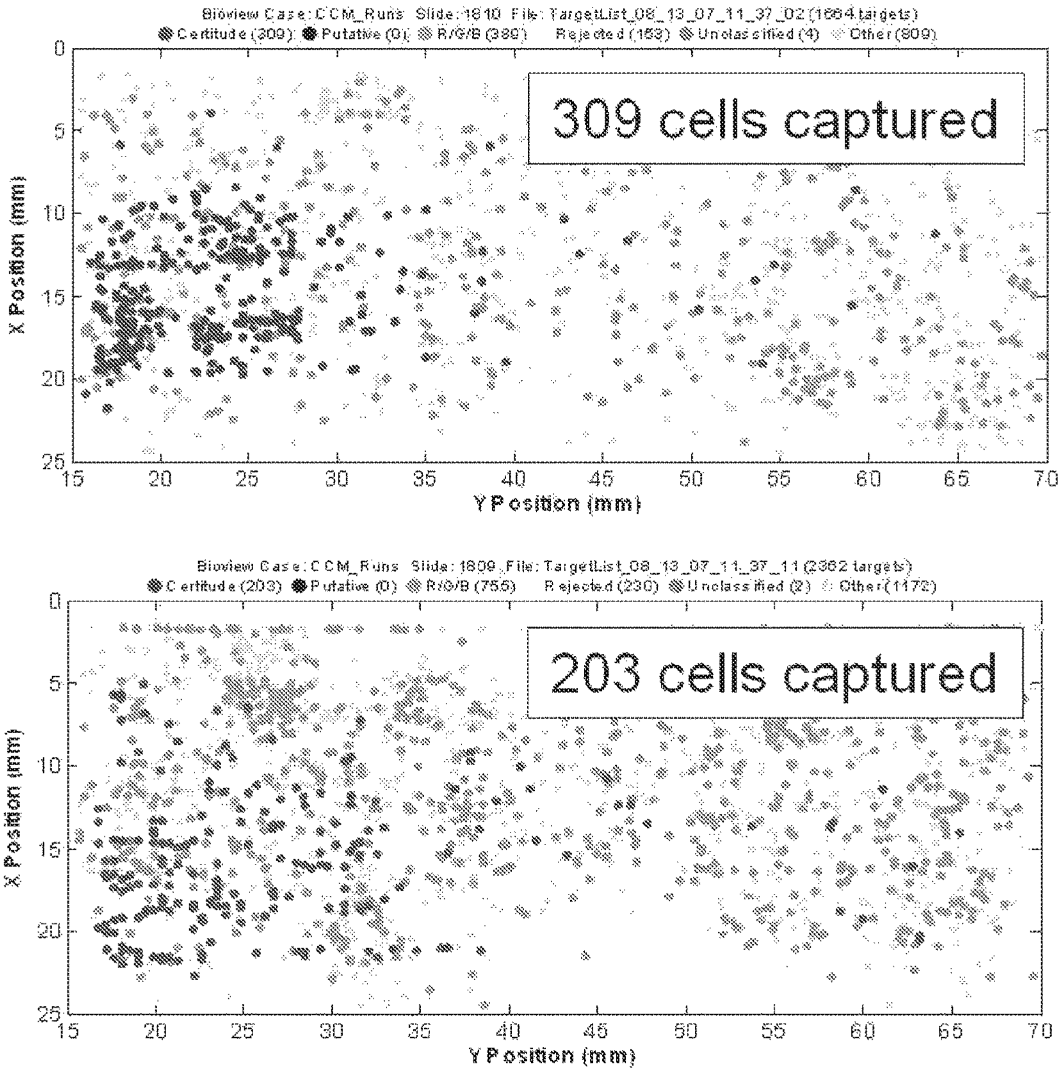
FIG. 1B depicts two fluorescent images illustrating the capture of lung cancer cells with biotinylated anti-EpCam antibody, an antibody that is specific for an epithelial cell marker present on lung cancer cells.

Example 1: Capture of H1650 Lung Cancer Cells with Biotinylated Anti-EpCam Antibody The example depicted in FIGS. 1A & 1B illustrates a method and device for isolating cancer cells. The affinity-tagged ligand (ATL) in this example comprised biotin as the affinity tag. The ligand was anti-Epithelial Cell Adhesion Molecule (EpCam) antibody which recognizes an epithelial cellular marker. For the experiment, H1650 lung cancer cells were incubated with biotinylated goat anti-EpCam antibody for 1 hour on ice (FIG. 1B). Approximately 1000 cells were input into each experiment. The left and right images represent replicate experiments. As a negative control, H1650 lung cancer cells were incubated with biotinylated goat IgG antibody under the same or similar conditions (FIG. 1A). Following the incubation, the cells were washed and run through an array of obstacles [comprising a restricted gap—Chip 7, please confirm] chip coated with Neutravidin™. Cells were then fixed and visualized by fluorescence microscopy.

The results of this experiment demonstrated that it is possible to use ATLs to isolate cancer cells. In this example, between 20 and 30% of the total H1650 lung cancer cell population were recovered when anti-EpCam antibody was used as the ligand. To calculate the percentage (%), the # of cells captured was divided by the total # of cells passed onto the chip, and the resulting value was multiplied by 100. In contrast, only 7-8% of cells were recovered when the goat IgG was used.

Figure 2A:
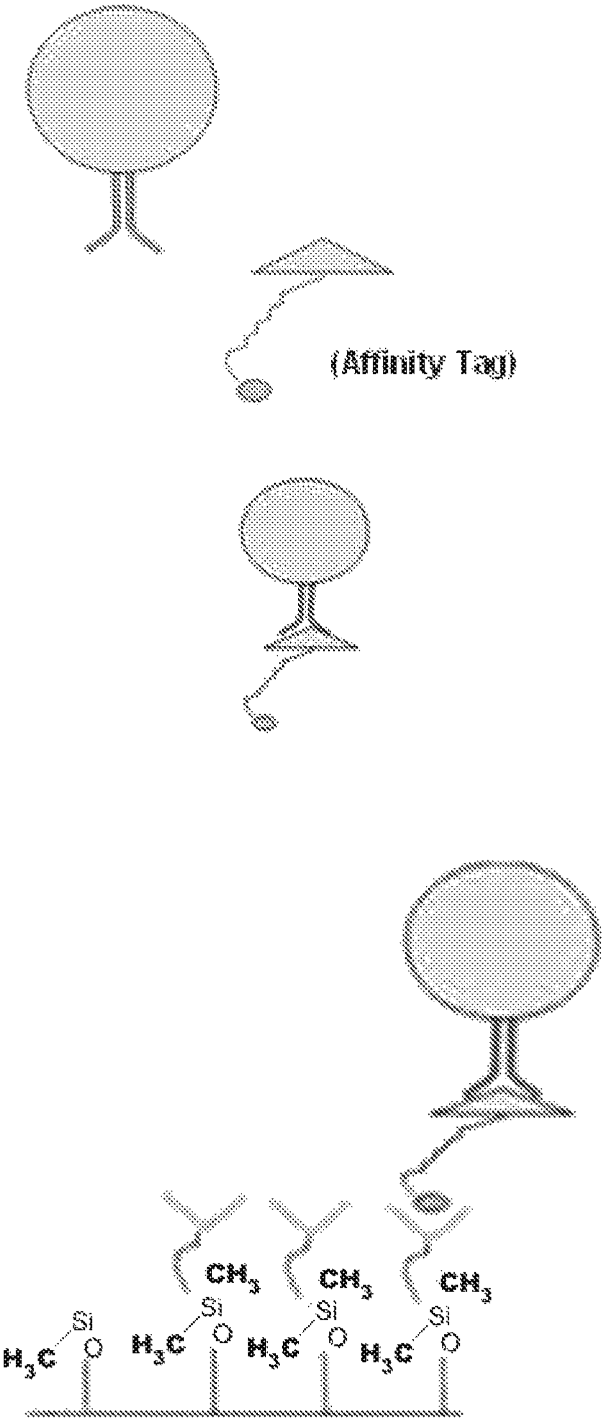
FIG. 2A is a diagram illustrating the capture of cells with a ligand tagged with an affinity tag such as biotin, histidine, or a magnetic particle (top panel), and the affinity-based capture of such cells using a microfluidic chip coated with a capture moiety capable of interacting with the affinity tag (bottom panel).
Figure 2B:
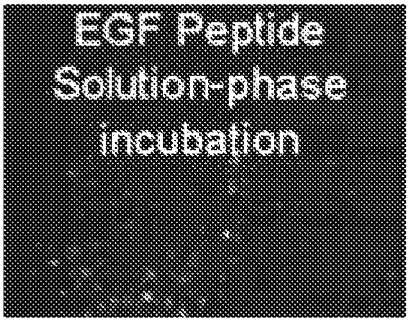
FIG. 2B is a fluorescent image illustrating the capture of cells bound to Biotin-tagged EGF using a microfluidic device coated with Avidin, a capture moiety capable of interacting with the affinity tag.

Example 2: Capture of Cells after Solution Phase Binding of the Cells with an Affinity-Tagged Ligand The examples depicted in FIGS. 2A & 2B illustrate the capture of cells labeled with an affinity tag before being subjected to a microfluidic device. FIG. 2A is a diagram depicting a cell being contacted with an affinity-tagged ligand in solution (top panel) and the capture of such cell with a microfluidic device coated with a capture moiety capable of recognizing the affinity-tag (lower panel).

FIG. 2B illustrates the capture of cells bound to EGF peptide tagged with biotin. In this example, MDA-MB-231 cells (a breast cell line which expresses low levels of EpCam) were contacted with biotin-tagged EGF peptide in solution under conditions favorable for binding. The cells were then subjected to a chip coated with neutravidin, a capture moiety capable of recognizing the affinity tag. Following fixation, the captured cells were visualized by fluorescent microscopy. The results demonstrate significant capture of cells using this method.

The invention claimed is:

1. A method for enriching rare analytes from a sample, comprising:

a) contacting said sample with an affinity-tagged ligand (ATL) complex wherein said ATL complex comprises:
   i) an affinity tag comprising a magnetic particle; and
   ii) at least a first ligand and a second ligand different from said first ligand, wherein said first ligand and said second ligand are linked to said affinity tag; and wherein said first ligand and said second ligand selectively bind different markers of said rare analytes, thereby labeling said rare analytes with said ATL complex;

b) flowing said sample comprising said ATL complex-labeled rare analytes through a microfluidic enrichment device comprising an array of obstacles, wherein said obstacles are arranged in rows offset from other obstacles to create restricted and expanded gaps and to thereby laterally displace ATL complex-labeled rare analytes based on their hydrodynamic size, and wherein at least some of said obstacles are coated or treated with one or more capture moieties that capture the labeled rare analytes;

wherein said capture moieties comprise a magnet or magnetized substrate that interacts with the magnetic particle of the affinity tag, to selectively enrich said labeled rare analytes.

2. The method of claim 1, wherein contacting said sample with an ATL complex is performed in solution.

3. The method of claim 1, wherein said affinity tag is linked to at least one of said first ligand and said second ligand via one or more linkers.

4. The method of claim 3, wherein said one or more linkers comprise at least one of: modified dextran; polyethylene glycol; polypropylene glycol; polyvinyl alcohol; polyvinylpyrrolidone; and polyethylene acrylamide.

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial sequence
<220> FEATURE:
<223> OTHER INFORMATION: Epidermal Growth factor (EGF) peptide

<400> SEQUENCE: 1

Tyr His Trp Tyr Gly Tyr Thr Pro Gln Asn Val Ile
1               5                   10


<210> SEQ ID NO 2
<211> LENGTH: 12
<212> TYPE: PRT
<213> ORGANISM: Artificial sequence
<220> FEATURE:
<223> OTHER INFORMATION: ligand epi peptide

<400> SEQUENCE: 2

Gln Met Ala Arg Ile Pro Lys Arg Leu Ala Arg His
1               5                   10
```

5. The method of claim 1, wherein said first ligand comprises a first antibody and said second ligand comprises a second antibody different from said first antibody.

6. The method of claim 5, wherein said first antibody binds to a first marker for said rare analytes and said second antibody binds to a second marker of said rare analytes, and wherein said first marker is different from said second marker.

7. The method of claim 5, wherein at least one of said first antibody and said second antibody is an Epithelial Cell Adhesion Molecule (EpCAM) antibody.

8. The method of claim 1, wherein said one or more markers comprise one or more cancer markers.

9. The method of claim 1, wherein said rare analytes comprise rare cells.

10. The method of claim 9, wherein said rare cells comprise circulating tumor cells.

11. The method of claim 1, wherein said sample comprises blood.

12. The method of claim 11, wherein said rare analytes comprise rare cells.

13. The method of claim 1, wherein said affinity tag reversibly binds to said capture moieties.

14. A method for enriching leukocytes or stem cells in a sample comprising:

a. contacting said sample with an affinity-tagged ligand (ATL) complex, wherein said ATL complex comprises:
   i. an affinity tag comprising a magnetic particle; and
   ii. at least a first ligand and a second ligand different from said first ligand, wherein said first ligand and said second ligand are linked to said affinity tag, and wherein said first ligand and said second ligand selectively bind different markers of said leukocytes or stem cells, thereby labeling said leukocytes or stem cells with said ATL complex;

b. flowing said sample comprising said ATL complex-labeled leukocytes or stem cells through a microfluidic device comprising an array of obstacles, wherein said obstacles are arranged in rows offset from other obstacles and that laterally displace the ATL complex-labeled leukocytes or stem cells based on their hydrodynamic size; and c. flowing said sample comprising said ATL complex-labeled specific cells that have been flowed through the microfluidic device in step b) through an enrichment device comprising a surface functionalized with a capture moiety, wherein said capture moiety comprises a magnet or magnetized substrate that interacts with the magnetic particle of the affinity tag on the ATL complex-labeled leukocytes or stem cells to selectively enrich said ATL complex-labeled specific cells.

15. The method of claim 14 wherein at least one ligand is an antibody.

16. The method of claim 15 wherein said antibody is an anti-leukocyte associated receptor antibody.

17. The method of claim 15 wherein at least one of said antibodies is an anti-leukocyte associated receptor antibody.

18. The method of claim 14, wherein both the first ligand and said second ligand are antibodies.

19. The method of claim 14, wherein said affinity tag is linked to at least one of said first ligand and said second ligand via one or more linkers.

20. The method of claim 19, wherein said one or more linkers comprise at least one of modified dextran, polyethylene glycol, polypropylene glycol, polyvinyl alcohol, polyvinylpyrrolidone, and polyethylene acrylamide.

* * * * *